(12) United States Patent
Abe et al.

(10) Patent No.: US 6,235,014 B1
(45) Date of Patent: May 22, 2001

(54) LASER TREATMENT APPARATUS

(75) Inventors: Hitoshi Abe, Okazaki; Yasuyuki Naito, Aichi; Kazunobu Kojima, Gamagori; Naho Kawai, Aichi, all of (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/281,273

(22) Filed: Mar. 30, 1999

(30) Foreign Application Priority Data

Mar. 31, 1998 (JP) .................................................. 10-125446
Mar. 31, 1998 (JP) .................................................. 10-125448

(51) Int. Cl.$^7$ .................................................. A61B 18/18
(52) U.S. Cl. .................................. 606/4; 606/12; 606/6; 345/20
(58) Field of Search .............................. 606/4–6, 10–12, 606/17; 345/20, 84, 112, 147, 339, 11, 12

(56) References Cited

U.S. PATENT DOCUMENTS

| | | | |
|---|---|---|---|
| 4,530,011 | * | 7/1985 | Haddick .............................. 358/244 |
| 4,597,649 | | 7/1986 | Swaniger et al. .................... 351/214 |
| 4,682,595 | * | 7/1987 | Hoerenz et al. .................. 128/303.1 |
| 4,702,576 | * | 10/1987 | Magnante ............................ 351/214 |
| 4,941,093 | * | 7/1990 | Marshall et al. ................ 364/413.01 |
| 5,098,426 | * | 3/1992 | Sklar et al. ............................. 606/5 |
| 5,196,006 | * | 3/1993 | Klopotek et al. ...................... 606/12 |
| 5,226,903 | * | 7/1993 | Mizuno ................................. 606/17 |
| 5,395,356 | * | 3/1995 | King et al. .............................. 606/4 |
| 5,470,329 | * | 11/1995 | Sumiya .................................... 606/4 |
| 5,480,396 | * | 1/1996 | Simon et al. ............................ 606/4 |
| 5,483,348 | * | 1/1996 | Komatsu et al. .................... 356/401 |
| 5,562,656 | * | 10/1996 | Sumiya .................................... 606/4 |
| 5,572,325 | * | 11/1996 | Komatsu et al. .................... 356/401 |
| 5,620,436 | * | 4/1997 | Lang et al. .............................. 606/4 |

FOREIGN PATENT DOCUMENTS

| | | |
|---|---|---|
| 0 400 470 | 12/1990 | (EP) . |
| 0 697 611 | 2/1996 | (EP) . |
| 0 729 734 | 9/1996 | (EP) . |
| 60-111627 | 6/1985 | (JP) . |
| 3-47278 | 2/1991 | (JP) . |
| 6-178761 | 6/1994 | (JP) . |
| 9-37196 | 2/1997 | (JP) . |
| WO 94/18883 | 9/1994 | (WO) . |

* cited by examiner

*Primary Examiner*—Linda C. M. Dvorak
*Assistant Examiner*—Ahmed Farah
(74) *Attorney, Agent, or Firm*—Finnegan, Henderson, Farabow, Garrett & Dunner, L.L.P.

(57) ABSTRACT

A laser treatment apparatus for performing treatments on a patient's eye by irradiating a laser beam is provided with an observation optical system including eyepieces through which a patient's eye is observed, wherein the brightness of a display part for displaying setting information such as laser irradiation conditions and others is controlled based on the light reception quantity detected by a light quantity detecting device.

11 Claims, 8 Drawing Sheets

LASER TREATMENT APPARATUS

BACKGROUND OF THE INVENTION

1. Field of the Invention

The present invention relates to a laser treatment apparatus for treating an affected part of a patient by irradiating a laser beam the affected part to be treated with a laser beam.

2. Description of Related Art

There have been known laser treatment apparatus for performing treatments by irradiating an affected part of a patient with a laser beam. In ophthalmic fields, those apparatus are used for photocoagulation treatments to be carried out on the affected part having various fundus diseases such as macular diseases (maculopathy), retinal detachment, etc. and on the peripheral part of the affected part, treatments of aftercataract (secondary cataract) which arises in posterior capsule of crystalline lens, and glaucoma treatments to be carried out by perforating, tapping or incising iris or angle of a patient's eye, and other treatments.

The above-mentioned typical laser treatments need a relatively and accurately specified irradiation spot. An operator therefore has to specify the irradiation spot during his magnification-observation of the patient's eye including the affected part through an observation optical system, and conducts the laser treatments. For the observation optical system, a slit lamp is generally used. In the laser treatments, the observation of the affected part illuminated by an illumination light are often performed in a state where the lightness of the using environment of the apparatus is lowered in order to reduce the influence of interference light from the surroundings of the apparatus, thereby to make easy to observe the interior of the patient's eye.

In the laser treatments, selecting or setting of the optimum parameter of laser beam's wavelengths, output power, and irradiation time, etc. is required according to each treatment's purpose, operational details, and the state of the patient's eye. To enable the operator to easily perform the above selection or settings, there has been known a laser treatment apparatus of a first type in which a control panel is disposed opposite to the operator, namely below eyepieces of the observation optical system. Usually, the control panel is provided with a display part using a light emitting element such as an LED to allow the operator to look set values.

There has been proposed a laser treatment apparatus of a second type that is provided with a control panel separately structured from the apparatus body, in which various information needed for treatments or observation of a patient's eye is displayed in a visual field of a finder of the slit lamp. The information is displayed optically or mechanically in the form of characters or numerals within the visual field viewed through the finder.

However, concerning the first type of the apparatus, when the environment's lightness is lowered to start laser treatment, operator's eyes receive the light from below because the display part of the control panel disposed directly below the eyepieces of the observation optical system is too bright with respect to the darkness of the using environment. Thus, the patient's eye including the affected part is not well observed by the operator due to the light from below. The operator, receiving such the dazzling light from below, can not concentrate his attention on the treatment operation, and needs a long time for alignment to specify the part to be treated. This may impose a burden on the patient's eye.

Furthermore, in using the apparatus of the first type, the operator must detach his eyes from the eyepieces of the slit lamp finder and look the settings displayed on the control panel to confirm as to whether or not the condition of the treatment laser beam is set in correspondence to the purpose of treatment to be carried out. Such the confirmation by the detachment of operator's eyes from the finder every time before the laser irradiation is troublesome for the operator. Meanwhile, the patient is kept waiting. The operator can not also concentrate his attention on the observation of the affected part of the patient's eye. If the operator does not detach his eyes from the finder during the laser treatment, he can not confirm whether the set condition of the treatment laser beam answers the treatment purpose.

In the case of the apparatus of the second type, the information is displayed at the constant brightness level within the visual field of the finder. According to the brightness of the observation visual field, which varies with the observed region of the patient's eye and the illumination light quantity, therefore, the observed region and the displayed information are hard to view. Specifically, the bright observation visual field causes difficulty in discriminating the displayed information, while the dark visual field gives a feeling of glaring to the operator's eyes and causes difficulty in viewing the observed region.

SUMMARY OF THE INVENTION

The present invention has been made in view of the above circumstances and has an object to overcome the above problems and to provide a laser treatment apparatus capable of improving visibility of information display and a region to be observed during a laser treatment, thereby to reduce a burden on a patient.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatments on a patient's eye by irradiating the eye with a laser beam, the apparatus comprising an observation optical system including eyepieces through which the patient's eye is observed by an operator, a setting device for setting irradiation conditions of the laser beam, a display part for displaying information of the irradiation conditions set by the setting device, a light detector for detecting a light quantity, and an adjuster for adjusting brightness of the display part based on the light quantity detected by the light detector.

The above apparatus may be arranged such that the display part is disposed near the eyepieces and the light detector detects a light quantity of an extraneous light with respect to the apparatus.

The above apparatus may also be arranged such that the display part displays the information of the irradiation conditions within an observation visual field viewed through the eyepieces, and the light detector detects a light quantity of a reflected light reflected by a portion of the patient's eye observed through the eyepieces.

Furthermore, the above apparatus may comprise a laser emitter for emitting a laser beam having a desired wavelength selected from a plurality of wavelengths, and the setting device may include a selector for selecting a wavelength of the laser beam to irradiate an affected part of the patient's eye, and the display part may display information of the wavelength of the laser beam selected by the selector within an observation visual field viewed through the eyepieces.

In the laser treatment apparatus of the present invention, the light quantity of the display part is controlled based on the light quantity of the light reflected by the part of the patient's eye or the extraneous light with respect to the apparatus. Accordingly, the displayed information and the observed part of the eye can be satisfactorily observed by the operator to make smooth alignment for laser treatment, and a burden on the patient's eye can be reduced.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
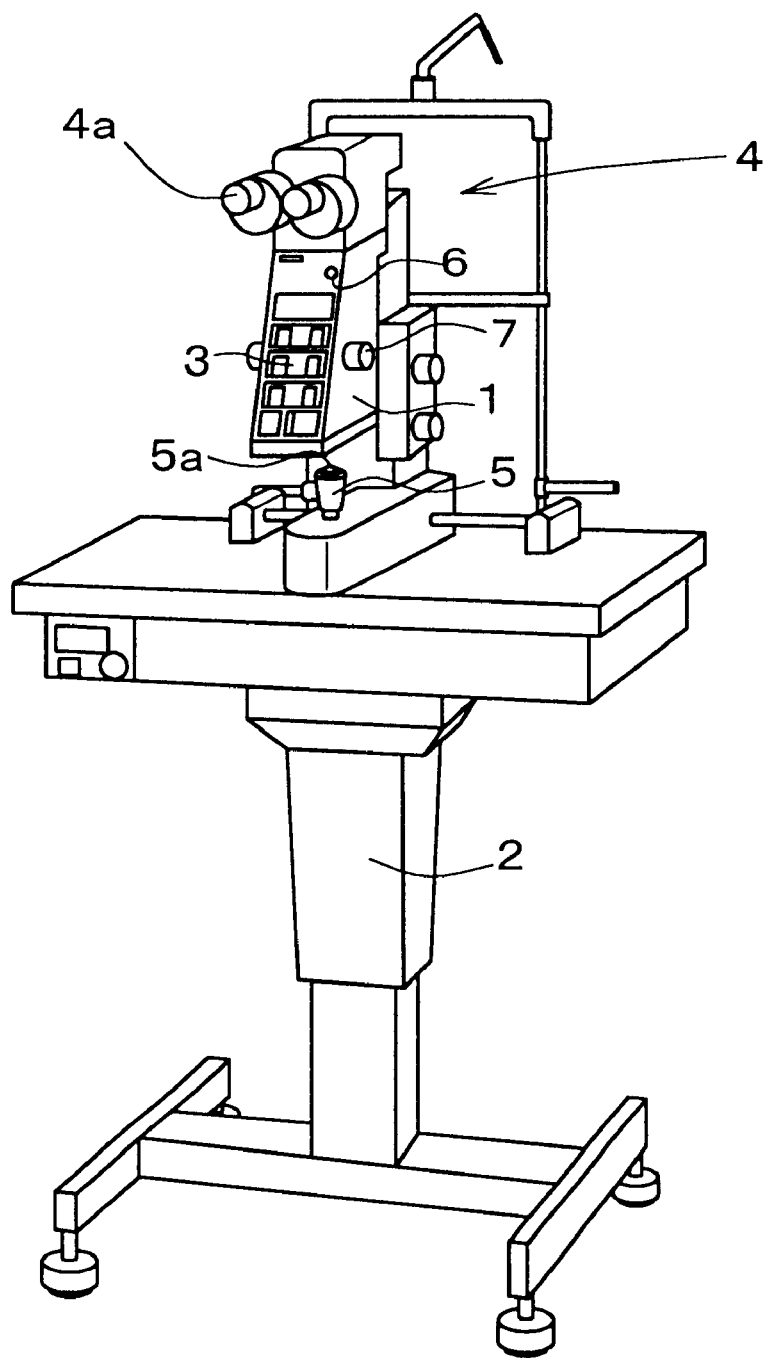
FIG. 1 is a schematic perspective view of a laser treatment apparatus in a first embodiment according to the present invention.
Figure 2:
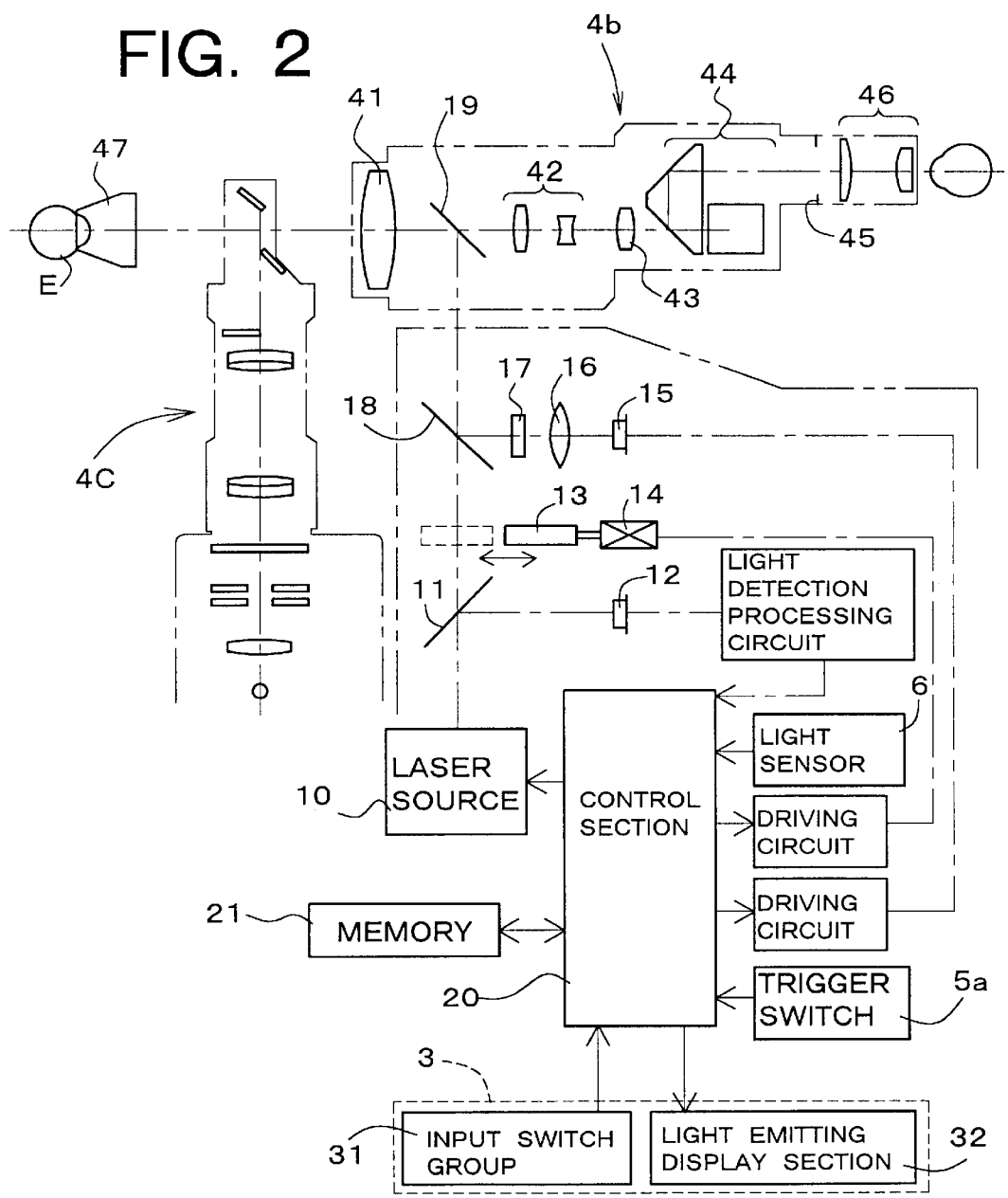
FIG. 2 is a schematic view showing the major components of a control system and an optical system of the laser treatment apparatus in the first embodiment.

A detailed description of preferred embodiments of a laser treatment apparatus embodying the present invention will now be given referring to the accompanying drawings. This laser treatment apparatus is used for performing aftercataract treatments and glaucoma treatments by the perforating, tapping or incising of iris and angle by the use of giant pulses. FIG. 1 is a schematic perspective view of the laser treatment apparatus. FIG. 2 is a schematic view of the major components of a control system and an optical system of the apparatus.

A laser oscillator 1 is provided with a treatment laser source 10, a light delivery optical system, and others. The laser source 10 has a solid laser rod, an optically pumped light source, and Q-switch, and others not shown. The laser source 10 can generates for a short time giant pulses which have a narrow pulse width and a large output peak. Used for the solid laser rod is an Nd:YAG rod which oscillates light having a basic wavelength of 1064 nm.

In the laser oscillator 1, there are provided a beam splitter 11, a light detector 12, a safety shutter 13, and a solenoid 14. The shutter 13 is insertable onto the optical axis of a laser beam from the laser source 10 thereby to ensure the safety at the time of the laser irradiation. Aiming light emitted from an aiming light source 15 using semiconductor laser is made into parallel luminous flux by a collimator lens 16, divided into two light beams by an aperture 17 formed with two holes. The light beams are reflected by a dichroic mirror 18 and delivered to a patient's eye E through a dichroic mirror 19 disposed in a slit lamp delivery 4 of which the details will be mentioned later.

Figure 3:
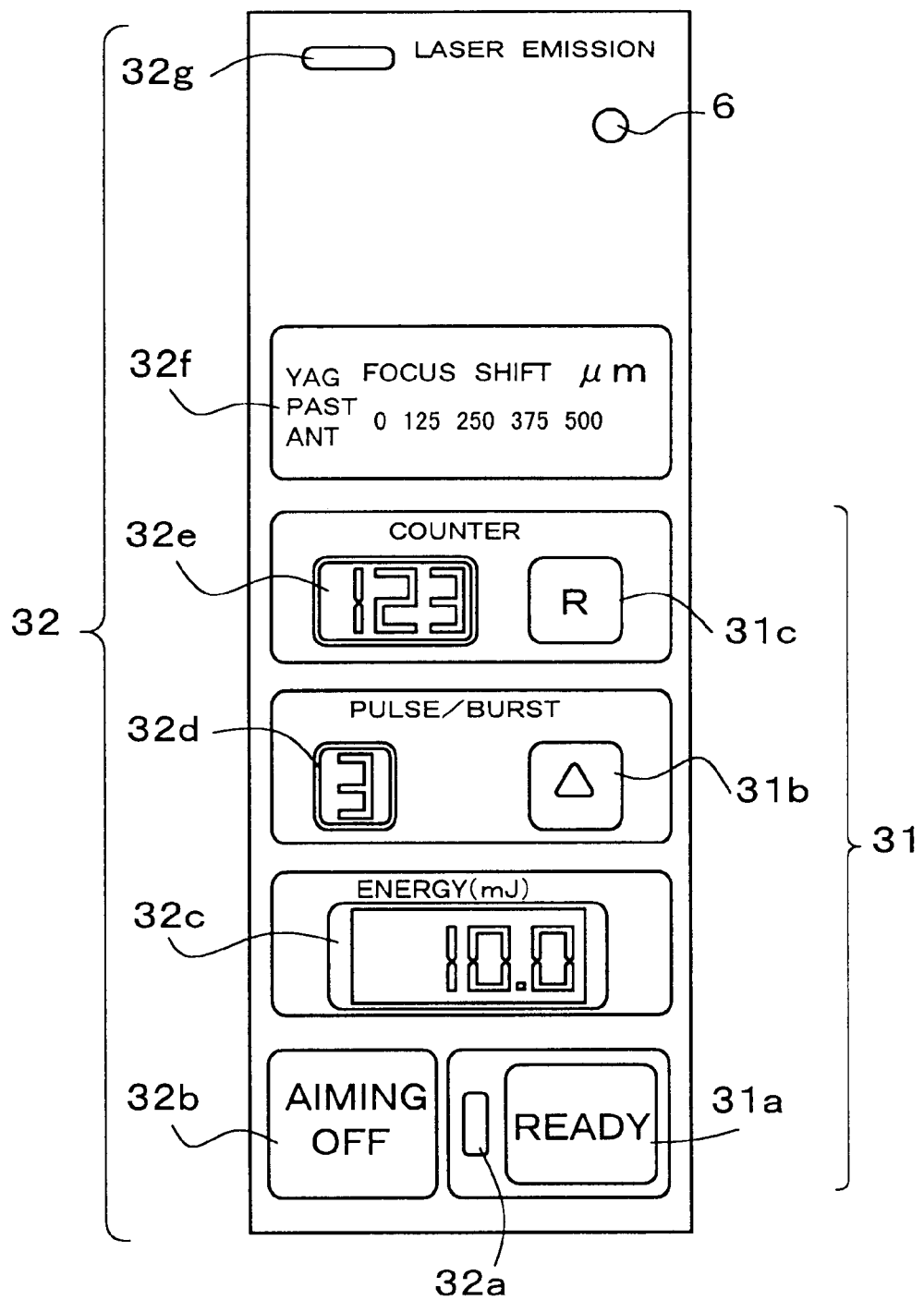
FIG. 3 is an illustration of the arrangement of switches and displays on a control panel of the laser treatment apparatus.

Numeral 2 is a stand which is vertically movable. Numeral 3 is a control panel for setting laser irradiation conditions. As shown in FIG. 3, the control panel 3 is provided with an input switch group 31 and a light emitting display section 32. FIG. 3 is an example of the arrangement of the switch group 31 and the light emitting display section 32 on the control panel 3.

The input switch group 31 includes a READY switch 31a for setting the laser irradiation ready state of the apparatus, a PULSE/BURST setting switch 31b for setting the number of laser irradiation in response to one trigger signal, and a COUNTER-RESET switch 31c for resetting a COUNTER display part 32e which displays the cumulative number of irradiation.

The display section 32 includes a READY lamp 32a for displaying the irradiation ready state of the apparatus, an AIMING-OFF lamp 32b for indicating a lighting-on/off of an aiming light, an ENERGY display part 32c for indicating the set intensity of laser energy, a PULSE/BURST display part 32d for displaying the number of irradiation set with the setting switch 31b, a COUNTER display part 32e for displaying the cumulative number of irradiation, a FOCUS-SHIFT display part 32f for displaying the amount of a shift of a focus point of a laser beam from a focus point of the aiming light, and a LASER-EMISSION Lamp 32g which is lighted when the power supply to the apparatus is turned on. The display section 32 displays the conditions, which are set through the switch groups 31 and an energy regulation knob 7, by the use of light emitting elements such as LED and the like.

Numeral 4 is a slit lamp delivery for observing the patient's eye E. While observing the eye E through this slit lamp delivery 4, the operator can perform laser irradiation to the affected part of the eye E through the laser oscillator 1. The slit lamp delivery 4 is structured of eyepieces 4a, a microscope part 4b which holds the observation optical system, and an illumination part 4c which holds the illumination optical system. The illumination part 4c can emit a spot light which is linearly changeable in diameter in a range of 0.2–8.0 mm. The microscope part 4b is provided with an objective lens 41 which is in common used between right and left observation optical paths, a variable magnification optical system 42, an image forming lens 43, erect prisms 44, a field stop 45, and an eyepiece 46, the elements from 42 to 46 being disposed in each of the right and left optical paths. The variable magnification optical system 42 is so constructed as to be properly switched according to a set magnification. When laser irradiation is carried out, an operator's safety filter is inserted onto the optical path between the lenses 41 and 43. A well known optical system is used for a structure of the illumination optical system of the illumination part 4c. The structure of this optical system is less related to the present invention and its detailed description is omitted in this specification.

Numeral 5 is a joystick for specifying the laser irradiation spot. Numeral 6 is a light sensor 6 for detecting the light quantity of an extraneous light. The joystick 5 is provided thereon with a trigger switch 5a for generating a trigger signal for laser irradiation. The light sensor 6 is disposed near the control panel 3.

Operation of the laser treatment apparatus constructed as above will be described hereinafter.

When the power supply to the apparatus is turned on by the operator, the lamp 32g is lighted and, after several seconds, test irradiation is started. The test irradiation is carried out in a state where the shutter 13 is inserted on the optical axis. The laser beam emitted from the laser light source 10 is reflected by the beam splitter 11 and enters the light detector 12. A control section 20 calculates the intensity of laser energy based on the light reception quantity detected by the light detector 12 to display the intensity on the display section 32c in 1/10 mJ (millijoule) unit. The test irradiation is conducted every time the energy intensity is set with the knob 7. The laser energy intensity detected by the detector 12 is each time displayed on the display section 32c.

Thereafter, by operating the switches 31 on the control panel and various setting knobs, the operator sets irradiation conditions including laser output energy, the number of irradiation pulses, and soon in response to the treatment purpose with respect to the patient's eye E.

If the above settings are made in a room illuminated with a bright light source such as a fluorescent light, the light sensor 6 detects a large quantity of light. The control section 20 thus controls the amount of current to be supplied to the display section 32 based on the light reception quantity by the sensor 6 so that the display section 32 is more lighted, thereby enabling the operator to easily confirm the setting conditions even in the lighted room.

Upon completion of the setting, the operator places the patient at a predetermined position and lowers the room's light which will become interference light, in order to ensure the easiness of observation of the part to be treated of the patient's eye E. The setting may be conducted in the room of which the light is lowered from the start.

When the room's light is lowered, the light reception quantity detected by the sensor 6 decreases. The control section reduces the amount of current to be supplied to the display section 32 in response to the light reception quantity, thereby to reduce the light quantity of display emitting elements and lowers the brightness level of the display section 32.

Figure 4A:
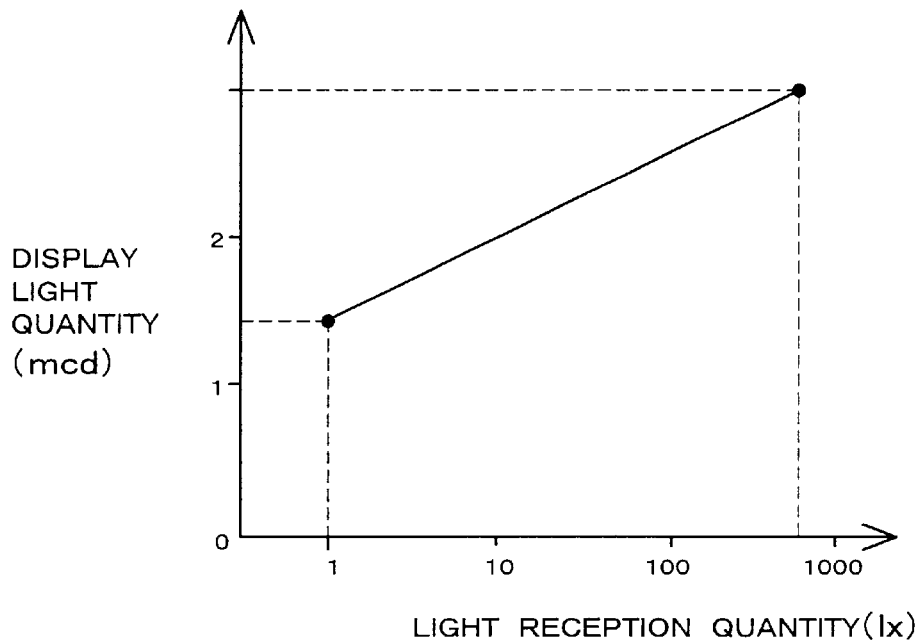
FIGS. 4(a) and 4(b) are graphs to explain the control of display light quantity with respect to light reception quantity.

The display light quantity of the display section 32 with respect to the ambient lightness is controlled in accordance with programs such as a table, a calculation expression, etc. stored in a memory 21 in advance. For instance, the display light quantity may be varied linearly in response to the light reception quantity by the light sensor 6, as shown in FIG. 4(a). Alternately, it may be varied in multiple steps in response to the light reception quantity as shown in FIG. 4(b).

Figure 4B:
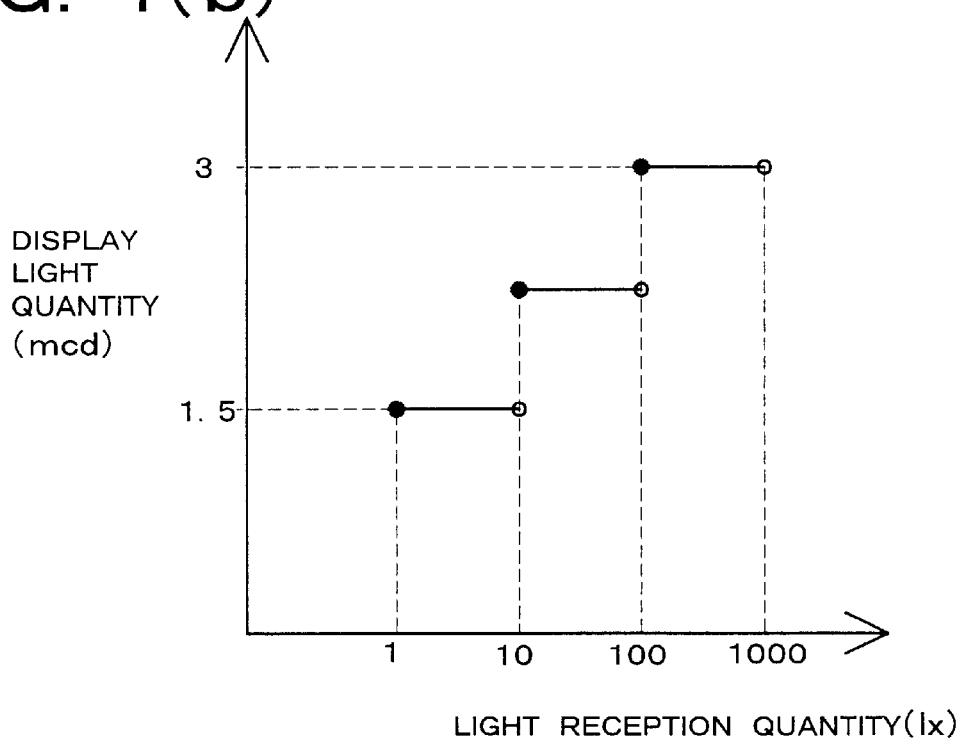

The horizontal axis of a graph shown in FIGS. 4(a) and 4(b) indicate the lightness (lux) of the room in logarithm table. The lightness of the room is generally 400–500 lux under a fluorescent light and 1–2 lux under dim light in a darkroom. The vertical axis of the graph shown in FIGS. 4(a) and 4(b) indicate the lightness of display (microradians), which is 3 mcd at the maximum and 1.5 mcd at the minimum by turning on the room's light at 50% of a duty ratio under duty control.

The operator performs alignment to adjust a sight of the aiming light to the affected part of the patient's eye E while observing the eye E through the observation optical system from the eyepieces 4a of the slit lamp delivery 4.

During the operator's observation of the affected part of the patient's eye E through the eyepieces 4a, the degree of the display light quantity of the display section 32 on the control panel 3 disposed just below the eyepieces 4a is reduced according to the ambient lightness. The light having high intensity is thus prevented from entering the operator's eyes during the observation. The operator can smoothly carry out the observation of the patient's eye E and the alignment of the aiming light.

The aiming light emitted from the light source 15 is delivered along the optical path mentioned above, divided into two beams, and the aiming light beams fall on the patient's eye E. The focal point of the treatment laser beam is shifted from an intersection point of the two aiming light beams by the distance indicated on the display section 32f. Referring to the intersection point information, the operator operates the joystick 5 to adjust the laser focal point to the affected part to accomplish the alignment.

The shifting of the laser focal point can be made by a well known zooming optical system.

After the completion of the alignment by the use of the aiming light, the operator depresses the trigger switch 5a to generate a trigger signal. Upon reception of the trigger signal, the control section 20 drives the solenoid 14 to cause the shutter 13 to retract from the laser optical axis and drives the laser source 10 to emit a laser beam.

The laser beam emitted from the laser source 10 is irradiated to the patient's eye E through the dichroic mirror 19 of the slit lamp delivery 4, causing tissue destruction due to the generation of plasma in the affected part, thereby performing treatment of the affected part.

The control section 20 causes the laser light source 10 to emit the laser beam based on the number of irradiation pulses set with the switch 31b.

Besides the above manner, various modifications are conceivable for the control of the display light quantity of the display section. If a plurality of extraneous light sensors are provided, for example, the display light quantity may be controlled in response to the mean value of the light reception quantity detected by the sensors or the maximum or minimum light reception quantity. Instead of the control of the whole display section, each display light quantity of the display parts may be controlled respectively.

Figure 5:
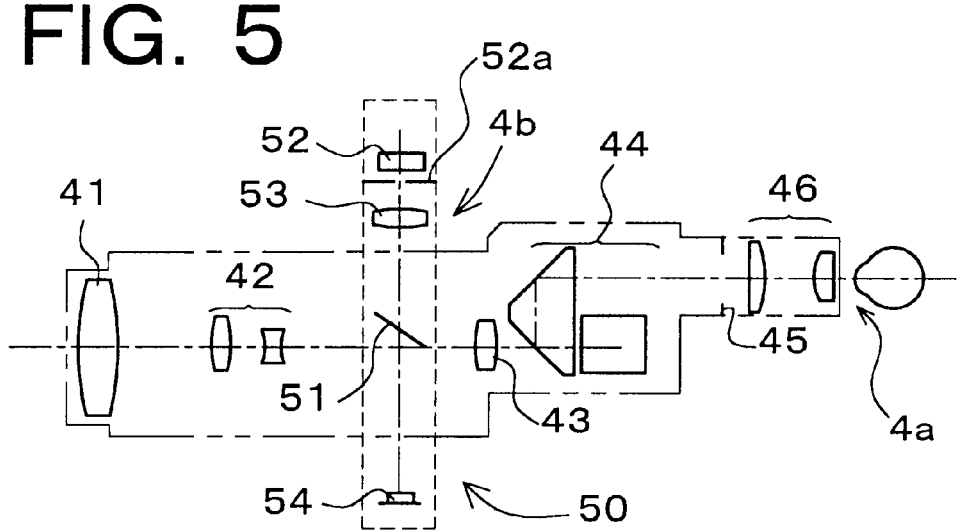
FIG. 5 is a schematic view showing the major components of an optical system of a microscope section of a laser treatment apparatus in a second embodiment.

Next, a second embodiment of the laser treatment apparatus according to the present embodiment will be explained. Like elements corresponding to those in the first embodiment are indicated by like numerals. In this second embodiment, the display section is provided within the microscope section of the slit lamp delivery, thereby enabling the operator to observe a display image within an observation visual field. FIG. 5 is a schematic view showing the major components of an optical system of a microscope section 4b holding the observation optical system.

As shown in FIG. 5, a display-in-visual-field system 50 is provided with a double-sided mirror 51 having both sides made of total reflection mirrors, disposed obliquely with respect to one of the optical paths and between the variable magnification optical system 42 and the lens 43. The variable magnification optical system 42 is alterable for 6 times magnification ratio and 40 times.

The mirror 51 is so formed as not to much shade an observation light. Above the mirror 51, there are provided a display section 52 using light emitting elements such as LED and a collimator lens 53. The display section 52 is disposed at a position with a conjugated relation to the field stop 45. That is, the display section 52 is positioned so that a stop 52a is focused on the operator's eyes. The display section 52 is also arranged such that the display luminous flux can be observed out of the center of the observation visual field due to the types and the arrangement position of the light emitting elements (see FIG. 6).

Below the mirror 51 is arranged a light sensor 54. When a part of the observation light reflected from the patient's eye E is reflected by the mirror 51, the sensor 54 detects the light quantity of the reflected light.

The laser apparatus in the second embodiment constructed as above can display the information within the observation visual field.

Operation of the apparatus in the second embodiment will be described hereinafter.

An operator makes a patient sit still in a predetermined position, and operates the joystick 5 to move the slit lamp delivery 4 so as to adjust a slit light from the illumination part 4c onto the eye E. After adjustment of the light quantity of the slit light and the focus, the operator sets a contact lens 47 on the patient's eye E and observes the affected part of the eye E through the eyepieces 4a. Prior to laser irradiation, the operator operates the switches on the control panel 3 to set various conditions including laser output energy and so on. The control section 20 controls the display section 52 in accordance with the set conditions.

Figure 6:
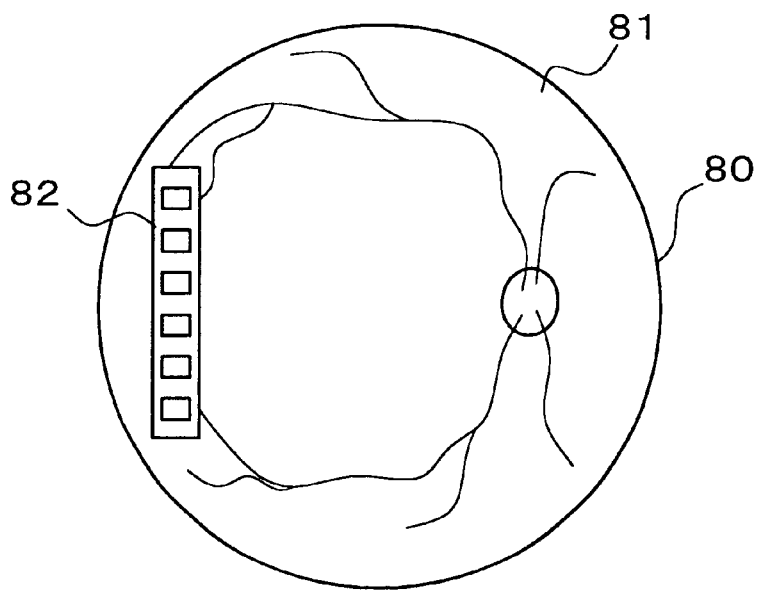
FIG. 6 is an illustration of a state of a visual field viewed through eyepieces of the optical system of the second embodiment.

FIG. 6 is an illustration of a state of the visual field viewed through the eyepieces 4a, looking the patient's eye E. Numeral 80 indicates a diameter of the visual field viewed through the eyepieces 4a. Numeral 81 indicates a fundus image of the eye E under observation. Numeral 82 is an image of the display section 52 displaying the set conditions. The brightness level of the display section 52 is determined based on the fundus-reflection light from the patient's eye E detected by the sensor 54. The illumination light from the illumination part 4c illuminates the eye fundus and the fundus-reflected light is then reflected by the mirror 51 toward the sensor 54. The sensor 54 detects the light quantity of the reflected light. The control section 20, serving as an adjusting device, adjusts the display light quantity of the display section 52 in response to a detection signal output from the sensor 54. Specifically, the display light quantity of the display section 52 is increased when the detection light quantity is large, while the display light quantity is decreased when the detection light quantity is small. It is to be noted that, similarly to in the first embodiment, variation in the display light quantity can be controlled linearly or in multiple steps by a function empirically found with respect to the variation in light quantity of the fundus-reflected light.

The display light quantity of the display-in-visual-field part is controlled as above in relation to the light quantity of the fundus-reflected light. At this time, the reflected light quantity and the display light quantity is maintained in a previously determined constant relation. Accordingly, the operator can satisfactorily observe both the information displayed within the visual field and the part to be observed (the eye fundus).

Figure 7:
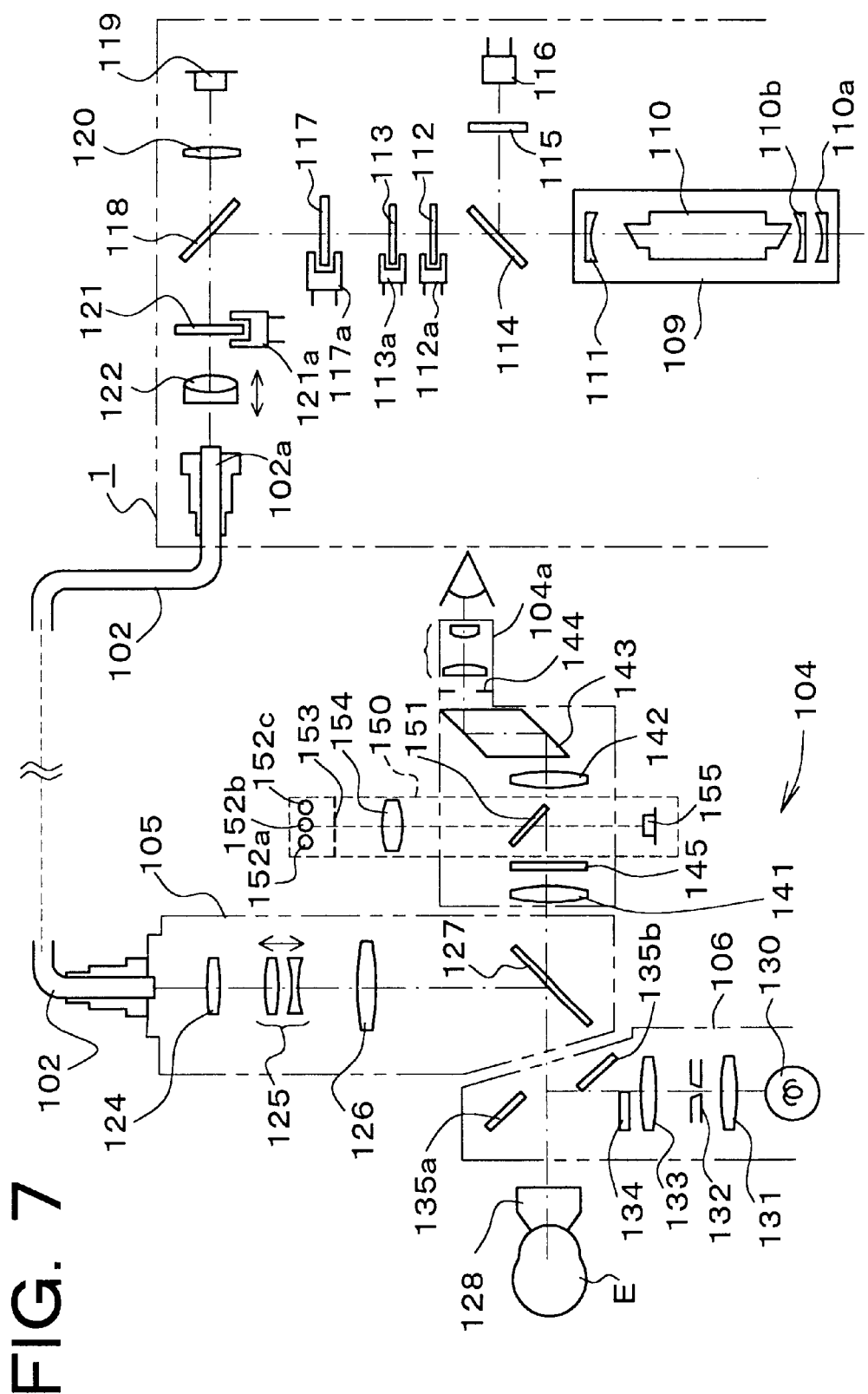
FIG. 7 is a schematic view showing the major components of an optical system of a laser treatment apparatus in a third embodiment.

Next, a third embodiment of the laser treatment apparatus according to the present invention will be explained. FIG. 7 is a schematic view showing the major components of an optical system of the laser treatment apparatus in the third embodiment.

A treatment laser source 109 is constructed of an ion laser tube 110, a first total reflection mirror 110a, a second total reflection mirror 110b, and an output mirror 111. In this embodiment, the laser tube 110 is a krypton laser (Kr) which oscillates red light with a wavelength of 647.1 nm, yellow light with a wavelength of 568.2 nm, and green light with wavelengths of 530.9 nm and 520.8 nm. The first total reflection mirror 110a has the property of reflecting yellow light and green light, and it is fixedly disposed on the laser optical axis. The second reflection mirror 110b has the property of reflecting red light, and it is disposed insertably onto the optical path. The output mirror 111 has the transmission rate of 1% to 3% for any of red light, yellow light, and green light with respective wavelength regions. Accordingly, when the second mirror 110b is positioned on the optical path, thus constructing a resonator in cooperation with the output mirror 111, and the resonator oscillates a red laser light. On the other hand, when the second mirror 110b is retracted from the optical path, the first mirror 110a constructs a resonator in cooperation with the output mirror 111, and the resonator oscillates an yellow laser light beam and a green laser light.

Numeral 114 is a beam splitter for allowing a large part of the laser beam from the laser source 109 to pass, while reflecting the other part of the laser beam. The laser beam reflected by the beam splitter 114 passes through a diffusion plate 115 and enters an output sensor 116. This sensor 116 detects the output energy of the laser beam emitted from the laser source 109.

Figure 8:
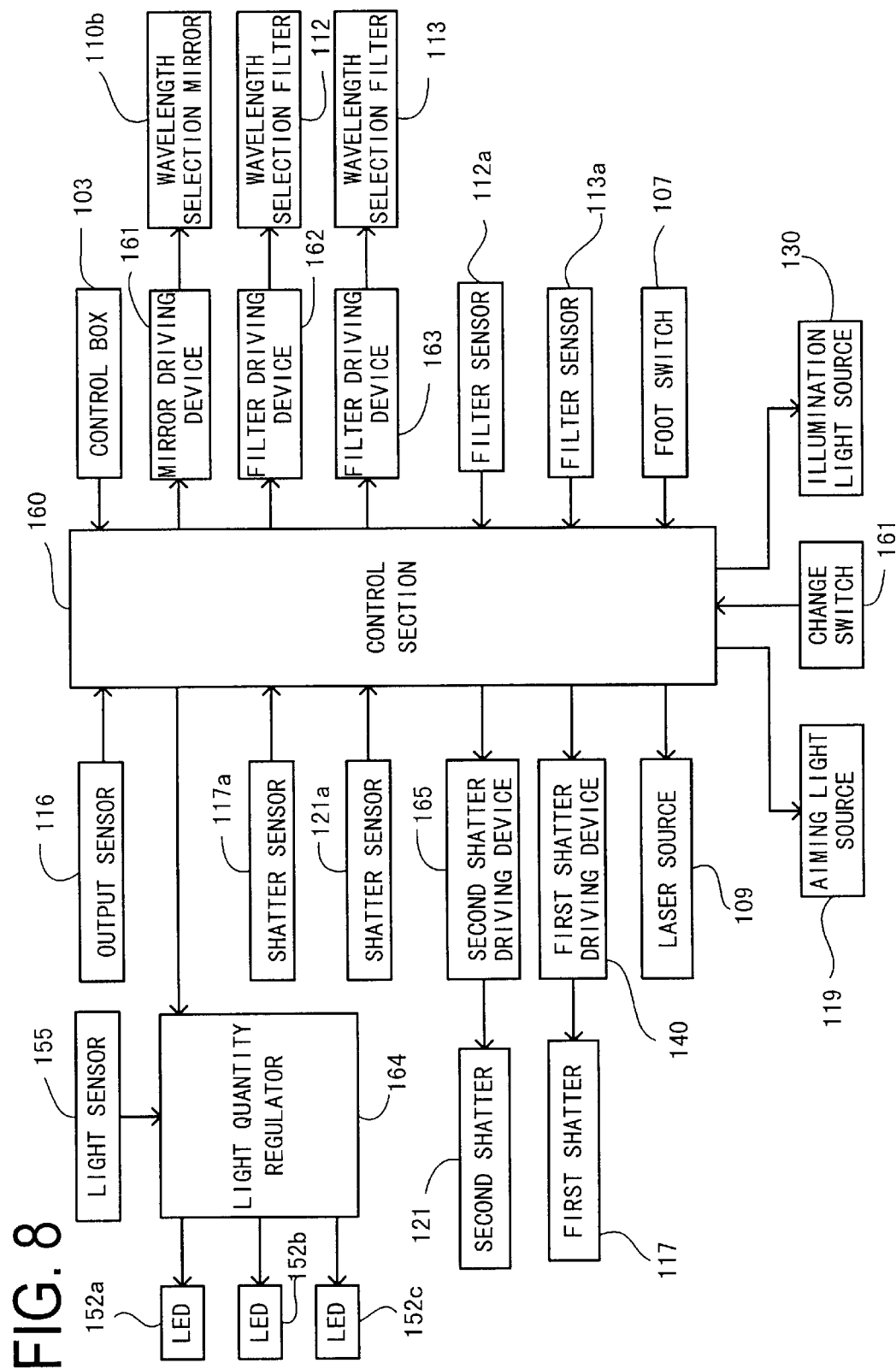
FIG. 8 is a block diagram of a control system of the laser treatment apparatus in the third embodiment.

Numeral 112 is a wavelength selection filter which selectively allows the green laser beam to pass. Numeral 113 is a wavelength selection filter which selectively the yellow laser beam to pass. Inserting either of the filter 112 or 113 onto the optical path furthermore makes it possible to chose any one of the laser beam with the yellow wavelength and the laser beam with the green wavelength both which are simultaneously emitted from the laser source 109. The wavelength selection filters 112 and 113 are inserted onto the optical path when filter driving devices 162 and 163 shown in FIG. 8 are operated. The inserted state of the filters 112 and 113 is checked by filter sensors 112a and 113a respectively.

A first safety shutter 117 is so arranged as to be retracted from the optical path by operation of a driving device 140 in response to the command signal of treatment laser irradiation, thereby to allow the laser beam to pass, while to be inserted onto the optical path in a predetermined case, e.g., when abnormal conditions are encountered. The open and closed state of the first safety shutter 117 is detected by a shutter sensor 117a.

Numeral 118 is a dichroic mirror. The red aiming laser beam emitted from a semiconductor laser 119 is made coaxial with the treatment laser beam through a collimator lens 120. A second safety shutter 121 is inserted onto the optical path while the semiconductor laser 119 does not emit the aiming laser beam. The open and closed state of the second shutter 121 is detected by a shutter sensor 121a. Disposed on the optical path is a condensing lens 122 that condenses the treatment laser beam and the aiming laser beam at an incident end 102a of an optical fiber 102 to cause the laser beam to enter therein.

The laser beam is delivered through the optical fiber 102 to a laser irradiation section 105. The laser beam then passes through a relay lens 124, a zooming lens 125 which is movable along the optical axis to vary a spot size of the laser beam, and an objective lens 126, and the laser beam is reflected by a total reflection mirror 127 toward the patient's eye E. The laser beam then irradiates the eye E through a contact lens 128 set on the eye E. The total reflection mirror 127 has the property of reflecting the treatment laser beam emitted from the laser source 109 and a part of the aiming laser beam emitted from the semiconductor laser 119, while allowing the observation light to pass.

An illumination light from an illumination light source 130 of an illumination section 106 is made into parallel luminous flux by a condenser lens 131 and illuminates a slit 132. After passed through the slit 132, the illumination light passes through a projection lens 133, and the light is reflected by split mirrors 135a and 135b and illuminates the patient's eye E through the contact lens 128. Numeral 134 is a correcting lens 134 for correcting a length of the optical path of the illumination light reflected by the splitting mirrors 135a and 135b. The light quantity of the illumination light source 130 can be adjusted consecutively and changeably by operation of a change switch 161.

A microscope section 104a is provided with an objective lens 141 which is in common used between the right and left observation optical paths, an image forming lens 142, an erect prism 143, a field stop 144, and an eyepiece 146, the elements from 142 to 146 being disposed in each of the right and left optical paths. When laser irradiation is carried out, an operator's safety filter 145 is inserted onto the optical path between the lenses 141 and 142.

A display section 150 is provided with a double-sided mirror 151 having both sides made of total reflection mirrors, disposed obliquely with respect to one of the observation optical paths and between the safety filter 145 and the image forming lens 142. The double-sided mirror 151 is so constructed as not to much shade an observation light. Above the mirror 151, there are provided an LED 152a which emits red light, an LED 152b which emits yellow light, an LED 152c which emits green light, a stop 153 positioned in conjugation with the field stop 144, and a collimator lens 154. The stop 153 is formed with three apertures arranged in correspondence with the three LEDs 152a, 152b, and 152c such that the display luminous flux from the LEDs 152a, 152b, and 152c may be observed respectively out of the center of the observation visual field (see FIG. 9). The form of the apertures is made quadrilateral to avoid the same form as a circular form of luminous flux of the aiming light.

A light sensor 155 is disposed below the double-sided mirror 151. A part of the observation light reflected by the patient's eye E is reflected by the mirror 151, and the light sensor 155 detects the light quantity of the reflected light.

Next, operation of the apparatus in the third embodiment will be explained with reference to a control block diagram of FIG. 8. An operator makes a patient sit still in a predetermined position, and operates the joystick 5 to move the slit lamp delivery 104 so as to adjust a slit light from the illumination part 106 onto the eye E. After adjustment of the light quantity of the slit light and the focus, the operator sets a contact lens 128 on the patient's eye E and observes the affected part of eye E through the microscope section 104a. Prior to laser irradiation, the operator operates switches on a control box 103 to set or select various conditions for laser irradiation such as laser beam's wavelength and output energy, and coagulation time, etc. The wavelength of the laser beam to be irradiated is selected from wavelength regions of red, yellow, yellowish green, and green to meet the treatment purpose. In response to the selection of the laser beam's wavelength, a control section 160 drives the mirror driving device 161 for causing the wavelength selection mirror 10b to be inserted onto or retracted from the optical path, and also drives the filter driving devices 162 and 163 to cause the wavelength selection filters 112 and 113 respectively to be inserted onto or retracted from the optical path, thereby setting a required optical system to obtain a laser beam with a selected wavelength. Simultaneously, in order to display the information of the type of the selected laser wavelength within in the visual field of the microscope section 104a, the control section 160 controls the LEDs 152a, 152b, and 152c in the following manner. If a red laser beam is selected, only the LED 152a is turned on. If an yellow laser beam is selected, only the LED 152b is turned on. If a green laser beam is selected, only the LED 152c is turned on. If an yellowish green laser beam is selected, the LED 152b for yellow light and the LED 152c for green light are turned on at the same time.

Figure 9:
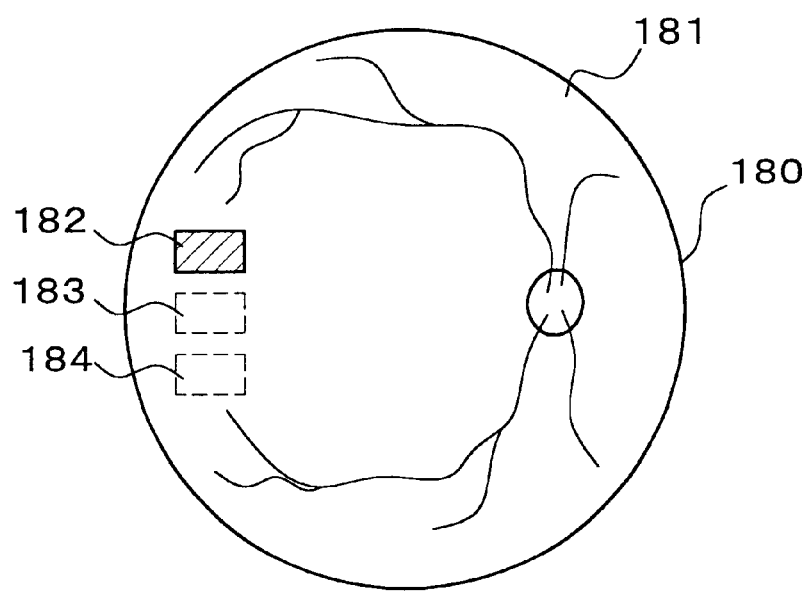
FIG. 9 is an illustration of a state of a visual field viewed through the optical system in a microscope section of the third embodiment.

FIG. 9 is an illustration of a state of a visual field viewed through the microscope section 104a of the third embodiment. Numeral 180 indicates a diameter of the visual field viewed through the microscope section 104a. Numeral 181 indicates an fundus image of the patient's eye E. A color information area 181 is projected with color when the LED 152a is turned on. A color information area 182 is projected with color when the LED 152b is turned on. A color information area 183 is projected with color when the LED 152c is turned on. When the LEDs are not turned on, those color information areas 182, 183, and 184 are not projected with color. This can avoid unnecessary shading of the visual field.

The light quantity of the LED's light to display the areas 182, 182, and 184 is determined based on the light quantity of the fundus-reflected light from the patient's eye E, the reflected light quantity being detected by the light sensor 155. Specifically, the illumination light from the illumination section 106 illuminates the eye fundus, and the fundus-reflected light passes through the total reflection mirror 127 and the objective lens 141, and the light is reflected by the doublesided mirror 151 toward the light sensor 151. This sensor 151 thus detects the light quantity of the reflected light. A light quantity regulation part 164 regulates the emission light quantity of the LEDs 152a, 152b, and 152c which are turned on in response to the detection signal output from the light sensor 155. Namely, the emission light quantity of the LEDs 152a–152c is increased when a detected light quantity is large, while it is lowered when the detected light quantity is small. The change in the emission light quantity is controlled linearly or in multiple steps by the function empirically found with respect to the variation in light quantity of the reflected light.

As a result of the above control of the display light quantity, the light quantity of the color information is immediately changed, for example, even when the illumination light quantity is changed by the change switch 161 in order to make easy to observe the affected part. The light quantity of the LEDs 152a, 152b, and 152c is retained in a previously determined constant relation to the light quantity of the reflected light from the eye fundus, thereby enabling the operator to satisfactorily observe both the information displayed within the visual field and the part to be observed (the eye fundus). The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for performing treatment on a patient's eye by irradiating the eye with a laser beam, the apparatus comprising:
- an observation optical system including eyepieces through which the patient's eye is observed by an operator;
- a setting device for setting irradiation conditions of the laser beam;
- a display part disposed proximate the eyepieces for displaying information of the irradiation conditions set by the setting device;
- a light detector disposed proximate at least one of the display part and the eyepieces for detecting a light quantity;and
- an adjustor for adjusting brightness of the display part based on the light quantity detected by the light detector.

2. The laser treatment apparatus according to claim 1, wherein the adjuster linearly adjusts the brightness of the display part based on the light quantity detected by the light detector.

3. The laser treatment apparatus according to claim 1, wherein the adjuster adjusts the brightness of the display part in steps of light quantity after dividing the light quantity detected by the light detector into multiple steps.

4. The laser apparatus according to claim 1, wherein the adjuster includes a memory for storing a program for adjusting the brightness of the display part based on the light quantity detected by the light detector.

5. A laser treatment apparatus for performing treatment on a patient's eye by irradiating the eye with a laser beam, the apparatus comprising:
- an observation optical system including eyepieces through which the patient's eye is observed by an operator;
- a setting device for setting irradiation conditions of the laser beam;
- a display part for displaying information of the irradiation conditions set by the setting device;
- a light detector for detecting a light quantity; and
- an adjustor for adjusting brightness of the display part based on the light quantity detected by the light detector;
- wherein the display part displays the information of the irradiation conditions within an observation visual field viewed through the eyepieces, and the light detector detects a light quantity of a reflected light reflected by a portion of the patient's eye observed through the eyepieces.

6. The laser treatment apparatus according to claim 5, wherein the adjuster linearly adjusts the brightness of the display part based on the light quantity detected by the light detector.

7. The laser treatment apparatus according to claim 5, wherein the adjuster adjusts the brightness of the display part in steps of light quantity after dividing the light quantity detected by the light detector into multiple steps.

8. The laser apparatus according to claim 5, wherein the adjuster includes a memory for storing a program for adjusting the brightness of the display part based on the light quantity detected by the light detector.

9. A laser treatment apparatus for performing treatment on a patient's eye by irradiating the eye with a laser beam, the apparatus comprising:
- a laser emitter for emitting the laser beam having a wavelength selected from a plurality of wavelengths;
- an observation optical system including eyepieces through which the patient's eye is observed by an operator;
- a setting device for setting irradiation conditions of the laser beam;
- a display part for displaying information of the irradiation conditions set by the setting device;
- a light detector for detecting a light quantity; and
- an adjustor for adjusting brightness of the display part based on the light quantity detected by the light detector;
- wherein the setting device includes a selector for selecting the wavelength of the laser beam to irradiate an affected part of the patient's eye; and
- the display part displays information of the wavelength of the laser beam selected by the selector within an observation visual field viewed through the eyepieces.

10. The laser treatment apparatus according to claim 9, wherein the wavelength information of the laser beam displayed by the display part includes predetermined different color information.

11. The laser treatment apparatus according to claim 9, further comprising:
- an aiming light emitter for emitting an aiming light beam used for setting the treatment laser beam at the affected part;
- wherein a form of the wavelength information of the laser beam is made into a different form from a form of the aiming light beam to be observed through the observation optical system.

* * * * *